United States Patent
Lieber et al.

(10) Patent No.: US 9,261,479 B2
(45) Date of Patent: *Feb. 16, 2016

(54) ELECTROCHEMICAL TEST SENSOR AND METHOD OF MAKING THE SAME

(71) Applicant: Bayer HealthCare LLC, Whippany, NJ (US)

(72) Inventors: Harris A. Lieber, White Plains, NY (US); Joseph E. Perry, Elkhart, IN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/529,749

(22) Filed: Oct. 31, 2014

(65) Prior Publication Data

US 2015/0052746 A1 Feb. 26, 2015

Related U.S. Application Data

(63) Continuation of application No. 12/746,803, filed as application No. PCT/US2008/085801 on Dec. 8, 2008.

(60) Provisional application No. 61/007,183, filed on Dec. 10, 2007.

(51) Int. Cl.
*G01N 27/327* (2006.01)
*G01N 33/487* (2006.01)

(52) U.S. Cl.
CPC ........ *G01N 27/3274* (2013.01); *G01N 27/3272* (2013.01); *G01N 33/48771* (2013.01)

(58) Field of Classification Search
CPC ........ G01N 27/327–27/3274; G01N 33/48771
See application file for complete search history.

(56) References Cited

U.S. PATENT DOCUMENTS

| 4,714,874 A | 12/1987 | Morris et al. |
| 5,281,395 A | 1/1994 | Markart et al. |

(Continued)

FOREIGN PATENT DOCUMENTS

| EP | 1 024 358 A | 8/2000 | ........... G01N 27/414 |
| EP | 1 152 239 A1 | 7/2001 | ........... G01N 27/327 |

(Continued)

OTHER PUBLICATIONS

Written Opinion corresponding to International Patent Application No. PCT/US2008/085801, European Patent Office, dated Mar. 19, 2009, 4 pages.

(Continued)

*Primary Examiner* — J. Christopher Ball
*Assistant Examiner* — Maris R Kessel
(74) *Attorney, Agent, or Firm* — Nixon Peabody LLP

(57) ABSTRACT

An electrochemical test sensor being adapted to assist in determining information relating to an analyte in a fluid sample and includes a base and a second layer. The base includes a plurality of electrodes, a working conductive lead and a counter conductive lead thereon. The electrodes include a working electrode and a counter electrode. The second layer assists in forming a channel in which the channel includes a reagent therein. Auto-calibration information of the test sensor is performed by a plurality of auto-calibration segments connected to one of the following: the working conductive lead, the counter conductive lead, or neither of the conductive leads, at least one of the plurality of auto-calibration segments being connected to the working conductive lead and at least one of the plurality of auto-calibration segments being connected to the counter conductive lead.

25 Claims, 12 Drawing Sheets

(56) References Cited

U.S. PATENT DOCUMENTS

| | | |
|---|---|---|
| 5,445,967 A | 8/1995 | Deuter |
| 5,510,266 A | 4/1996 | Bonner et al. |
| 5,575,403 A | 11/1996 | Charlton et al. |
| 5,856,195 A | 1/1999 | Charlton et al. |
| 5,863,800 A | 1/1999 | Eikmeier et al. |
| 6,599,406 B1 | 7/2003 | Kawanaka et al. |
| 6,814,844 B2 | 11/2004 | Bhullar et al. |
| 7,212,925 B2 | 5/2007 | Genshaw |
| 7,316,929 B2 | 1/2008 | Purcell |
| 2003/0013941 A1 | 1/2003 | Cohn et al. |
| 2004/0019653 A1 | 1/2004 | Debaty et al. |
| 2004/0019686 A1 | 1/2004 | Toyoda et al. |
| 2004/0156832 A1 | 8/2004 | Jolly |
| 2004/0178066 A1 | 9/2004 | Miyazaki et al. |
| 2004/0200721 A1 | 10/2004 | Bhullar et al. |
| 2004/0244151 A1 | 12/2004 | Sakata et al. |
| 2005/0016845 A1 | 1/2005 | Groll et al. |
| 2005/0016846 A1 | 1/2005 | Groll et al. |
| 2005/0019805 A1 | 1/2005 | Groll et al. |
| 2005/0019945 A1 | 1/2005 | Groll et al. |
| 2005/0019953 A1 | 1/2005 | Groll |
| 2005/0023137 A1 | 2/2005 | Bhullar et al. |
| 2005/0076845 A1 | 4/2005 | Langdale |
| 2005/0079945 A1 | 4/2005 | Wittkopp |
| 2005/0161345 A1 | 7/2005 | Groll et al. |
| 2005/0168747 A1 | 8/2005 | Fox |
| 2005/0226846 A1 | 10/2005 | Umlauf et al. |
| 2005/0279647 A1 * | 12/2005 | Beaty ............................ 205/792 |
| 2006/0189895 A1 | 8/2006 | Neel et al. |
| 2007/0110615 A1 | 5/2007 | Neel et al. |
| 2008/0105024 A1 | 5/2008 | Creaven et al. |
| 2008/0254544 A1 | 10/2008 | Modzelewski et al. |
| 2009/0028964 A1 | 1/2009 | Muni et al. |
| 2009/0030617 A1 | 1/2009 | Schell et al. |
| 2009/0113981 A1 | 5/2009 | Beer |
| 2009/0125268 A1 | 5/2009 | Perry |
| 2009/0301166 A1 | 12/2009 | Charlton et al. |
| 2010/0017165 A1 | 1/2010 | Zhong |
| 2010/0084466 A1 | 4/2010 | Charlton et al. |

FOREIGN PATENT DOCUMENTS

| | | | | |
|---|---|---|---|---|
| EP | 1 256 798 A1 | 11/2002 | ........... | G01N 27/327 |
| EP | 1 431 758 A | 6/2004 | ........... | G01N 27/447 |
| EP | 1 475 630 A1 | 11/2004 | ........... | G01N 27/28 |
| WO | WO 2004 113914 A1 | 12/2004 | ........... | G01N 33/487 |
| WO | WO 2004 113915 A1 | 12/2004 | ........... | G01N 33/487 |
| WO | WO 2005 001474 A1 | 1/2005 | ........... | G01N 33/487 |
| WO | WO 2006 035322 A2 | 4/2006 | | |
| WO | WO 2006 113723 A2 | 10/2006 | ............. | G01N 33/53 |
| WO | WO 2006 113865 A2 | 10/2006 | | |
| WO | WO 2010 048277 A2 | 4/2010 | ............. | G01N 21/27 |

OTHER PUBLICATIONS

International Search Report corresponding to International Patent Application No. PCT/US2008/085801, European Patent Office, dated Mar. 19, 2009, 4 pages.

Office Action in corresponding European Patent Application No. 08 860 676.9-1240, dated Nov. 8, 2010 (4 pages).

Office Action in corresponding European Patent Application No. 08 860 676.9-1240, dated May 12, 2011 (3 pages).

* cited by examiner

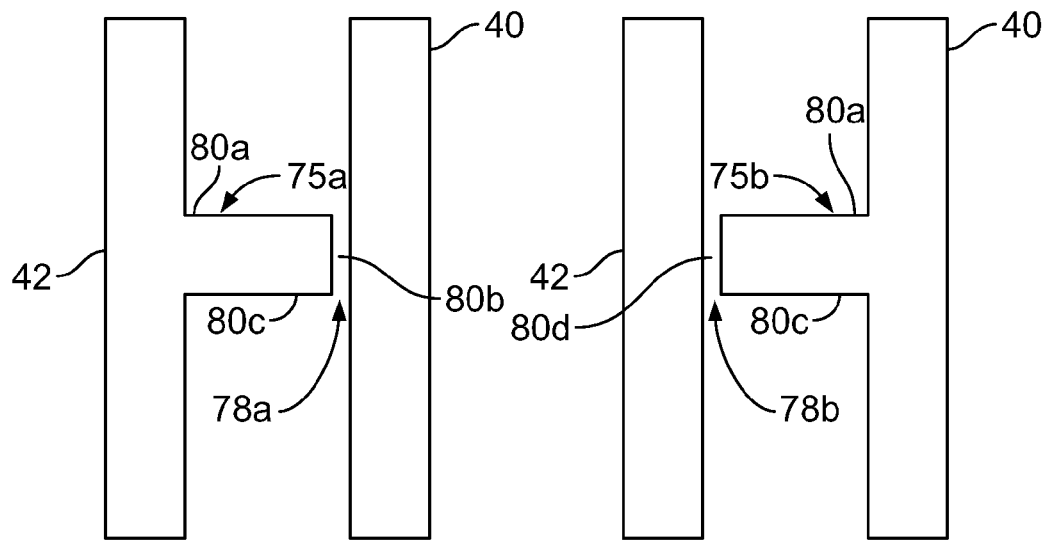
FIG. 3A      FIG. 3B
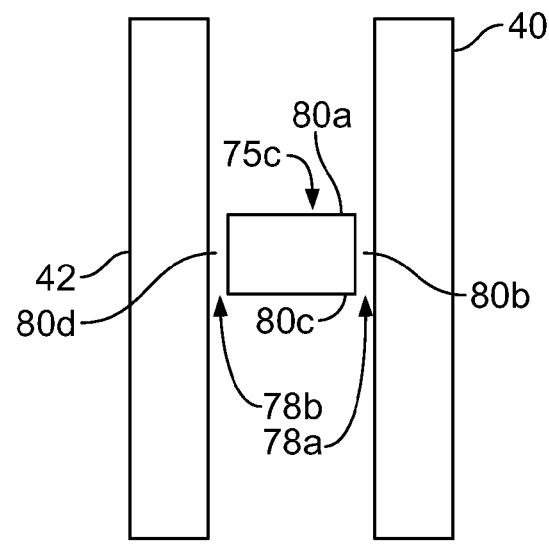
FIG. 3C

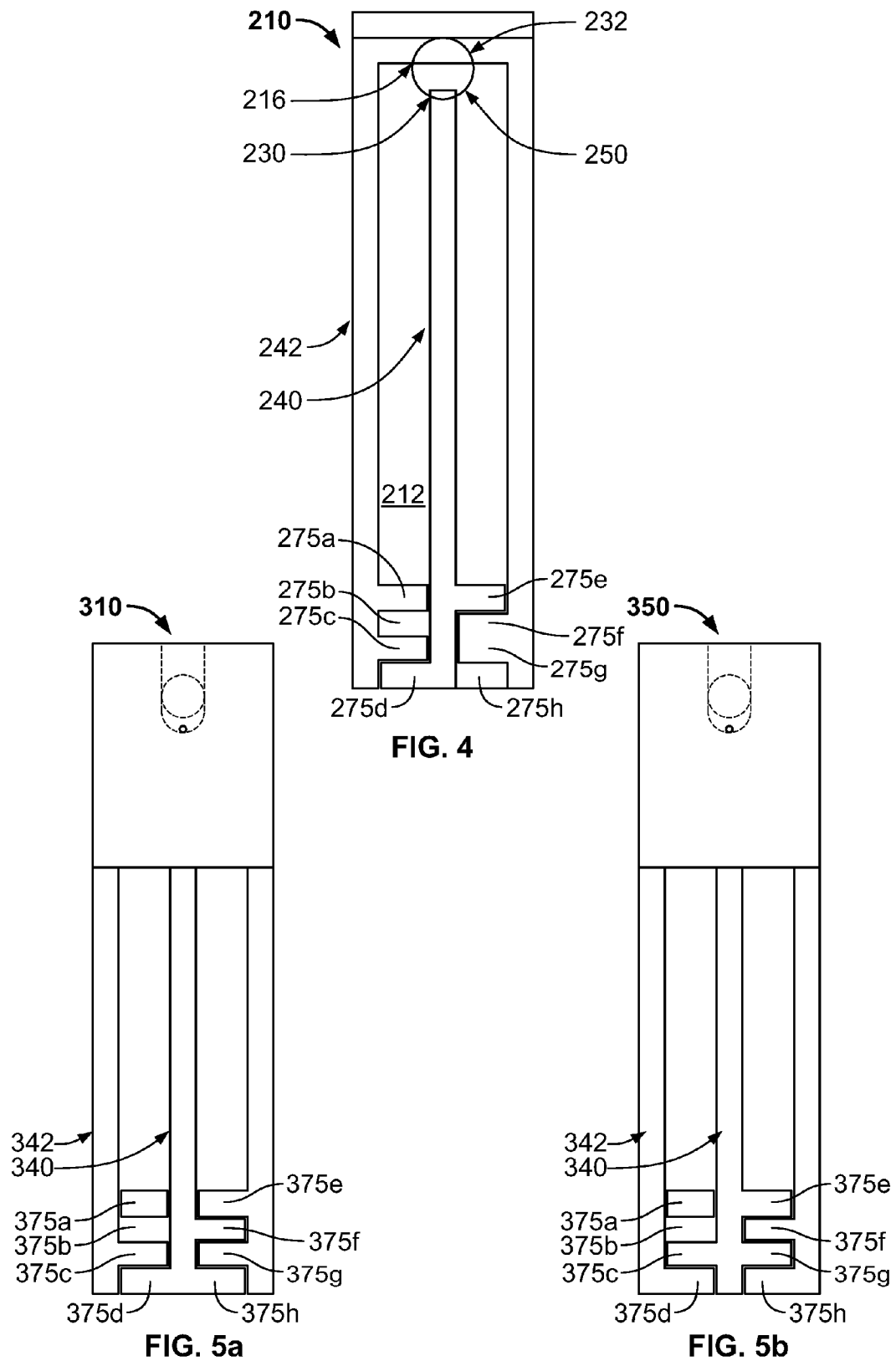

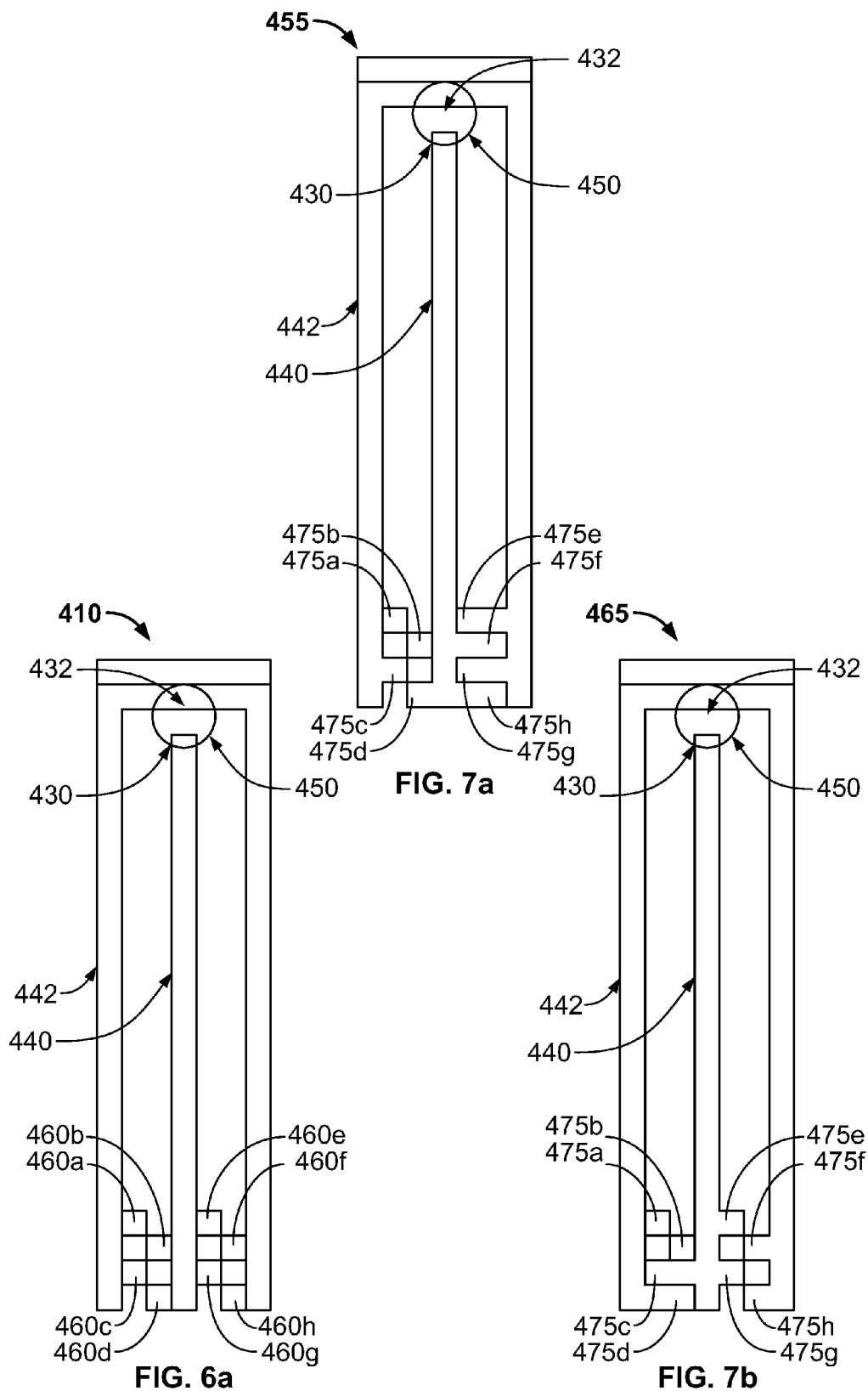

US 9,261,479 B2

ELECTROCHEMICAL TEST SENSOR AND METHOD OF MAKING THE SAME

CROSS REFERENCE TO RELATED APPLICATIONS

This application is a continuation of application Ser. No. 12/746,803 filed Jun. 8, 2010, which has been allowed; application Ser. No. 12/746,803 is a nationalized application of Application No. PCT/US2008/085801 filed Jun. 8, 2008, which claims priority to Application No. 61/007,183, which are all incorporated by reference in their entireties.

FIELD OF THE INVENTION

The present invention relates generally to test sensors that are adapted to determine an analyte concentration. More specifically, the present invention generally relates to auto-calibrating test sensors.

BACKGROUND OF THE INVENTION

The quantitative determination of analytes in body fluids is of great importance in the diagnoses and maintenance of certain physical conditions. For example, lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with, for example, blood glucose. The testing end of the sensor is adapted to be placed into the fluid being tested, for example, blood that has accumulated on a person's finger after the finger has been pricked. The fluid may be drawn into a capillary channel that extends in the sensor from the testing end to the reagent material by capillary action so that a sufficient amount of fluid to be tested is drawn into the sensor. The tests are typically performed using optical or electrochemical testing methods.

Diagnostic systems, such as blood-glucose testing systems, typically calculate the actual glucose value based on a measured output and the known reactivity of the reagent-sensing element (e.g., test sensor) used to perform the test. The reactivity or lot-calibration information of the test sensor may be provided on a calibration circuit that is associated with the sensor package or the test sensor. This calibration circuit is typically physically inserted by the end user. In other cases, the calibration is automatically done using an auto-calibration circuit via a label on the sensor package or the test sensor. In this case, calibration is transparent to the end user and does not require that the end user insert a calibration circuit into the meter. This assists in reducing calibration error by the user. Manufacturing millions of sensor packages, each having a calibration circuit or label to assist in calibrating the sensor package, can be expensive.

Therefore, it would be desirable to have a test sensor that provides calibration information thereon that may be manufactured in an efficient manner and that is easily used by the user.

SUMMARY OF THE INVENTION

According to one method, an electrochemical test sensor adapted to assist in determining information relating to an analyte in a fluid sample is formed. A base and a second layer to assist in forming a channel are provided. A plurality of electrodes on the base including a working electrode and a counter electrode is provided. Working and counter conductive leads that are electrically connected to the respective working and counter electrode are provided. Reagent formed in the channel is provided. Auto-calibration information of the test sensor is provided by forming a plurality of auto-calibration segments to be connected to one of the following: the working conductive lead, the counter conductive lead, or neither of the conductive leads. At least one of the plurality of auto-calibration segments is connected to the working conductive lead and at least one of the plurality of auto-calibration segments is connected to the counter conductive lead.

According to one embodiment, an electrochemical test sensor is adapted to assist in determining information relating to an analyte in a fluid sample. The test sensor comprises a base and a second layer. The base includes a plurality of electrodes, a working conductive lead and a counter conductive lead thereon. The plurality of electrodes includes a working electrode and a counter electrode. The second layer assists in forming a channel. The channel includes a reagent therein. Auto-calibration information of the test sensor is determined by including the use of a plurality of auto-calibration segments connected to one of the following: the working conductive lead, the counter conductive lead, or neither of the conductive leads. At least one of the plurality of auto-calibration segments being connected to the working conductive lead and at least one of the plurality of auto-calibration segments being connected to the counter conductive lead.

BRIEF DESCRIPTION OF THE DRAWINGS

FIG. 1b is a side view of the electrochemical test sensor of FIG. 1a.

FIG. 1c is a top view of the base to be used in the electrochemical test sensor depicting a plurality of auto-calibration areas of FIG. 1a.

FIG. 2b is a side view of the electrochemical test sensor of FIG. 2a.

FIGS. 3a-3c are enlarged top views showing different types of auto-calibration segments having been formed.

FIG. 4 is a top view of an electrochemical test sensor without a lid depicting auto-calibration segments according to one embodiment.

FIGS. 5a, 5b are top views of an electrochemical test sensor depicting auto-calibration segment complements according to one embodiment.

FIG. 6a is a top view of an electrochemical test sensor depicting a plurality of auto-calibration areas of FIG. 1a according to a further embodiment.

FIGS. 7a, 7b are top views of an electrochemical test sensor depicting auto-calibration segment compliments according to one embodiment.

DETAILED DESCRIPTION OF ILLUSTRATED EMBODIMENTS

Generally, an instrument or meter uses a test sensor adapted to receive a fluid sample to be analyzed and a processor adapted to perform a predefined test sequence for measuring a predefined parameter value. A memory is coupled to the processor for storing predefined parameter data values. Calibration information associated with the test sensor may be read by the processor before or after the fluid sample to be measured is received, but not after, for example, the analyte concentration has been determined. Calibration information is generally used to compensate for different characteristics of test sensors, which will vary on a batch-to-batch basis. In some systems, the calibration information is provided on an auto-calibration circuit or label that is associated with each test sensor batch.

The calibration information may be, for example, the lot specific reagent calibration information for the test sensor. The calibration information may be in the form of a calibration code. Selected information associated with the test sensor (which may vary on a batch-to-batch basis) is tested to determine the calibration information to be used in association with the meter.

The electrochemical test sensors are adapted to receive a fluid sample and be analyzed using an instrument or meter. The test sensor assists in determining information related to the analytes such as analyte concentrations. Analytes that may be measured include glucose, cholesterol, lipid profiles, microalbumin, urea, creatinine, creatine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

In one embodiment, the electrochemical test sensor includes at least a base, a plurality of electrodes, and a second layer such as a lid and/or a spacer. In one embodiment, the electrochemical test sensors include a base, a plurality of electrodes and a lid. In another embodiment, the electrochemical test sensors include a base, a plurality of electrodes, a spacer and a lid.

The base, spacer and lid may be made from a variety of materials such as polymeric materials. Non-limiting examples of polymeric materials that may be used to form the base, spacer and lid include polycarbonate, polyethylene terephthalate (PET), polystyrene, polyimide, and combinations thereof. It is contemplated that the base, spacer and lid may be independently made of other materials. The electrode pattern may be made from a variety of conductive materials including, but not limited to, gold, platinum, rhodium, palladium, ruthenium, carbon or combinations thereof.

Figure 1A:
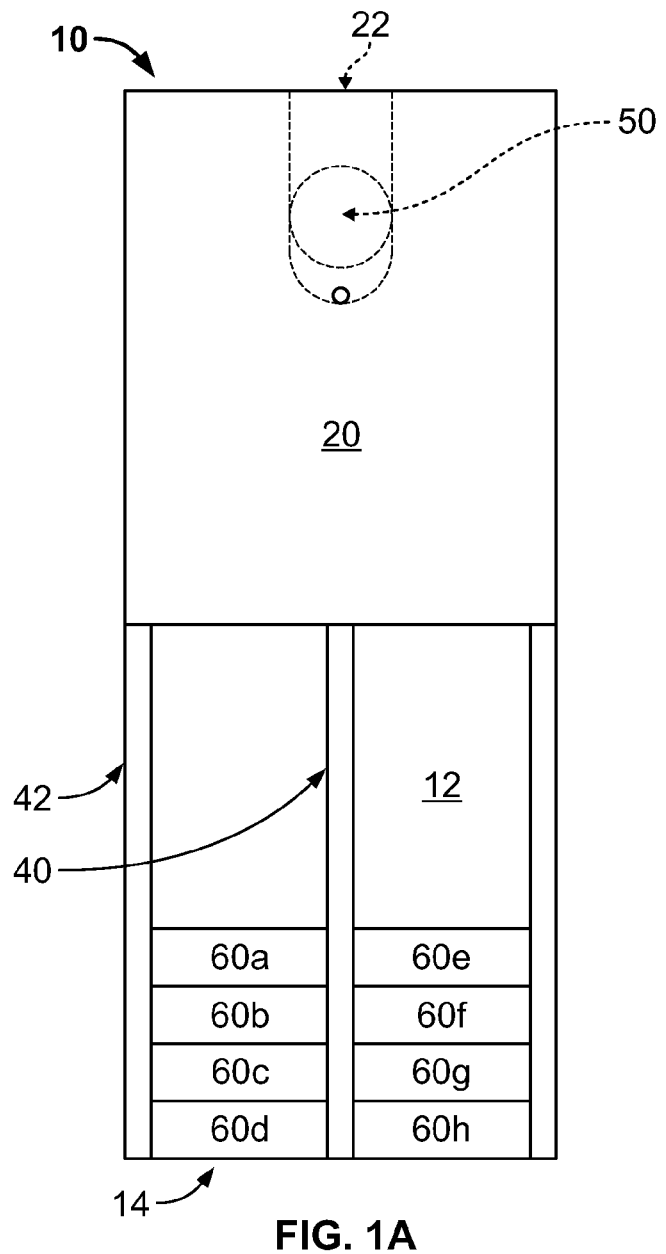
FIG. 1a is a top view of an electrochemical test sensor according to one embodiment.
Figure 1B:
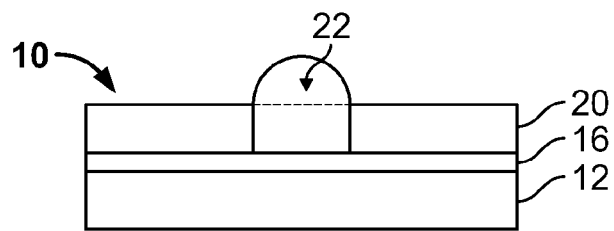
Figure 1C:
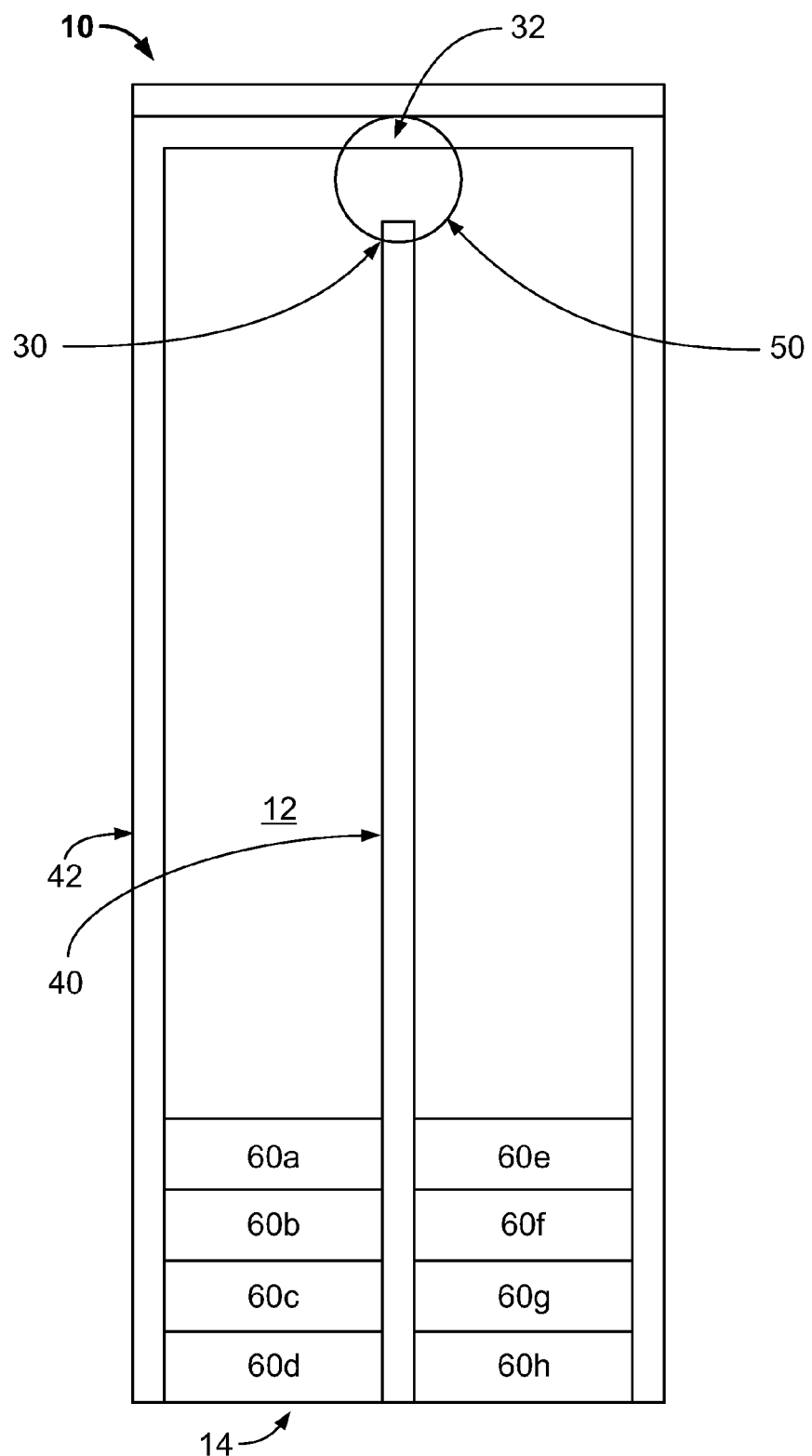

One non-limiting example of an electrochemical test sensor is shown in FIGS. 1a-1c. FIGS. 1a, 1b depict an electrochemical test sensor 10 that includes a base 12, an electrochemically-active layer 16, and a lid 20. In this embodiment, the electrochemically-active layer 16 is adapted to form a plurality of electrodes. It is contemplated that the plurality of electrodes may be formed without the use of a initial layer that covers the base.

FIG. 1c depicts the electrochemically-active layer 16 without a lid. Referring back to FIG. 1b, a channel 22 (e.g., capillary channel) is formed when the base 12, the electrochemically-active layer 16 and the lid 20 are attached to each other. The capillary channel 22 provides an enclosed flow path for introducing the sample into the test sensor 10 and eventually contacting the electrodes 30, 32 and, thus, forms a reaction zone.

As shown in FIG. 1a, the test sensor 10 includes a reactive or fluid-receiving area 50 that contains an enzyme. The enzyme is selected to react with the desired analyte or analytes to be tested so as to assist in determining an analyte concentration of a fluid sample. The reactive area 50 includes a reagent for converting an analyte of interest (e.g., glucose) in a fluid test sample (e.g., blood) into a chemical species that is electrochemically measurable, in terms of the electrical current it produces, by the components of the electrode pattern.

The reagent typically contains an enzyme (e.g., glucose oxidase), which reacts with an analyte (e.g., glucose) and with an electrochemical mediator (e.g., ferricyanide) to produce an electrochemically measurable species that can be detected by the electrodes. The reactive area 50 may comprise a polymer, an enzyme, and an electron acceptor. The reactive area 50 also may include additional ingredients such as a buffer and a surfactant in some embodiments of the present invention. It is contemplated that other enzymes may be used to react with glucose such as glucose dehydrogenase. One type of glucose dehydrogenase is FAD-GDH. If the concentration of another analyte is to be determined, an appropriate enzyme is selected to react with the analyte.

In one embodiment, the electrochemically-active layer 16 as shown in FIG. 1c forms a plurality of electrodes 30, 32, a plurality of conductive leads or traces 40, 42 and a plurality of auto-calibration areas 60a-h. It is contemplated that the size and shape of the auto-calibration areas may vary from that depicted in FIG. 1c.

The plurality of electrodes of FIG. 1c includes at least a counter electrode 30 and a working electrode 32 according to this embodiment. The working electrode measures the current when a potential is applied across the working and counter electrodes. The counter electrode should be sufficiently large so as to support the reaction occurring at the working electrode. The applied voltage may be referenced to the reagent deposited adjacent to the counter electrode. The conductive leads 40, 42 assist in establishing electrical communication between the respective electrodes 30, 32 and the auto-calibration segments that will be eventually formed from the auto-calibration areas 60a-h. The auto-calibration segments or pads are electrically connected with meter contacts (not shown) and assist in conveying auto-calibration information of the analyte to the meter. It is also contemplated that the auto-calibration segments may also convey information to assist in determining the analyte concentration.

In addition to the counter electrode 30 and the working electrode 32, other electrodes such as a trigger electrode may be used in forming the plurality of electrodes on an electrochemical test sensor. It is contemplated that other electrodes may be used. For example, an electrochemical test sensor may include a detection electrode that detects an underfill condition. The electrochemical test sensor may also include a hematocrit electrode that assists in correcting for the bias that occurs with selected hematocrit concentrations. Additional electrodes include, but are not limited to, electrodes that detect other analytes or species that may potentially interfere with the measurement of the desired analyte. Also, a second working electrode that assists in determining the concentration of another analyte may be used.

It is contemplated that more or less electrodes may be formed in the electrochemical test sensor. For example, the electrochemical test sensor may include exactly two electrodes or at least three electrodes. The exactly two electrodes may be a working electrode and a counter electrode in which an electrochemically created current flow when these electrodes are electrically connected and a potential is created between them. The electrodes are formed of conductive materials such as, for example, metallic materials (e.g., gold, platinum, palladium, rhodium, ruthenium, or combinations thereof) or carbon.

Figure 1D:
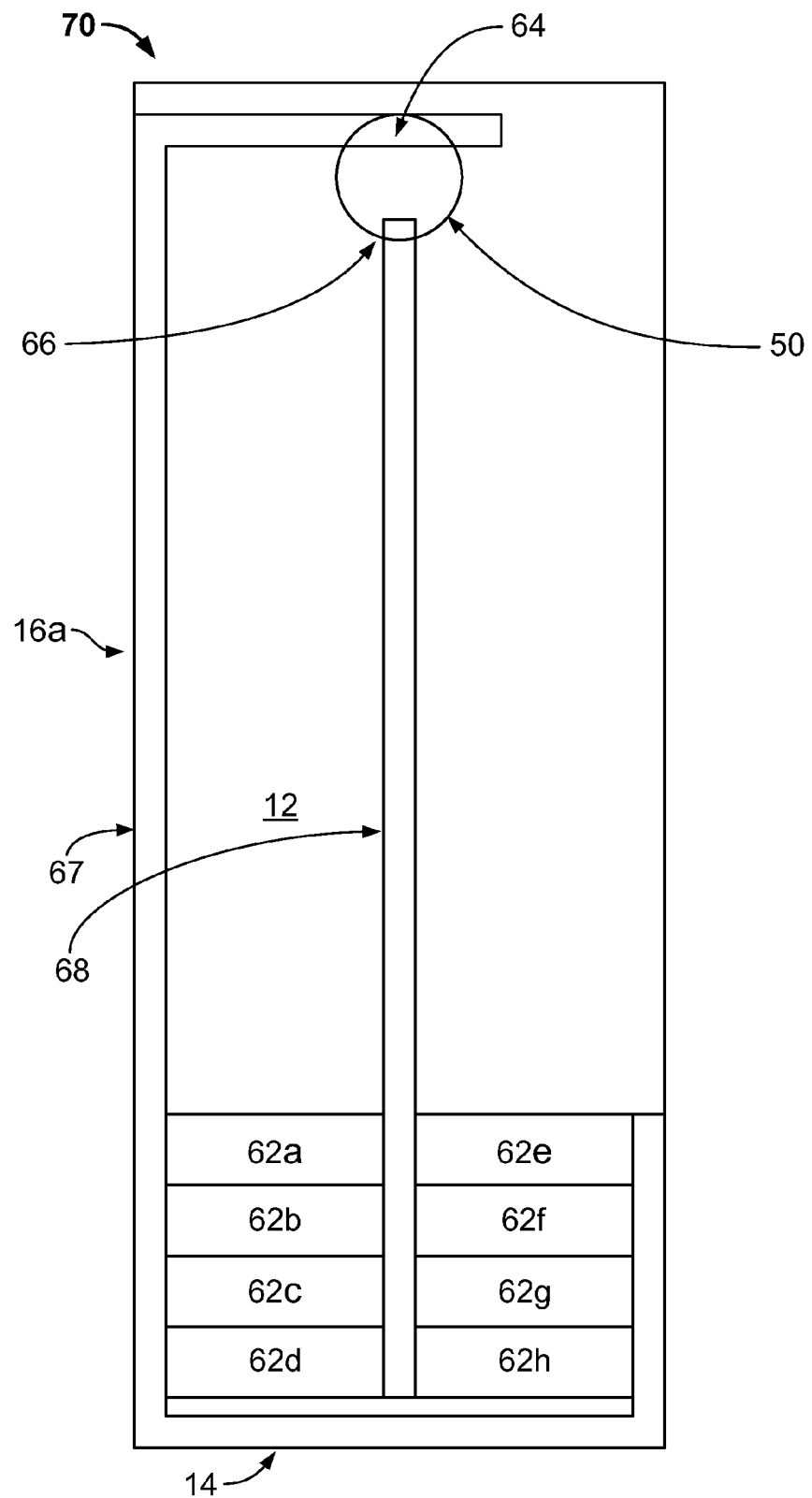
FIG. 1d is a top view of the base to be used in the electrochemical test sensor depicting a plurality of auto-calibration areas according to one embodiment.
Figure 1E:
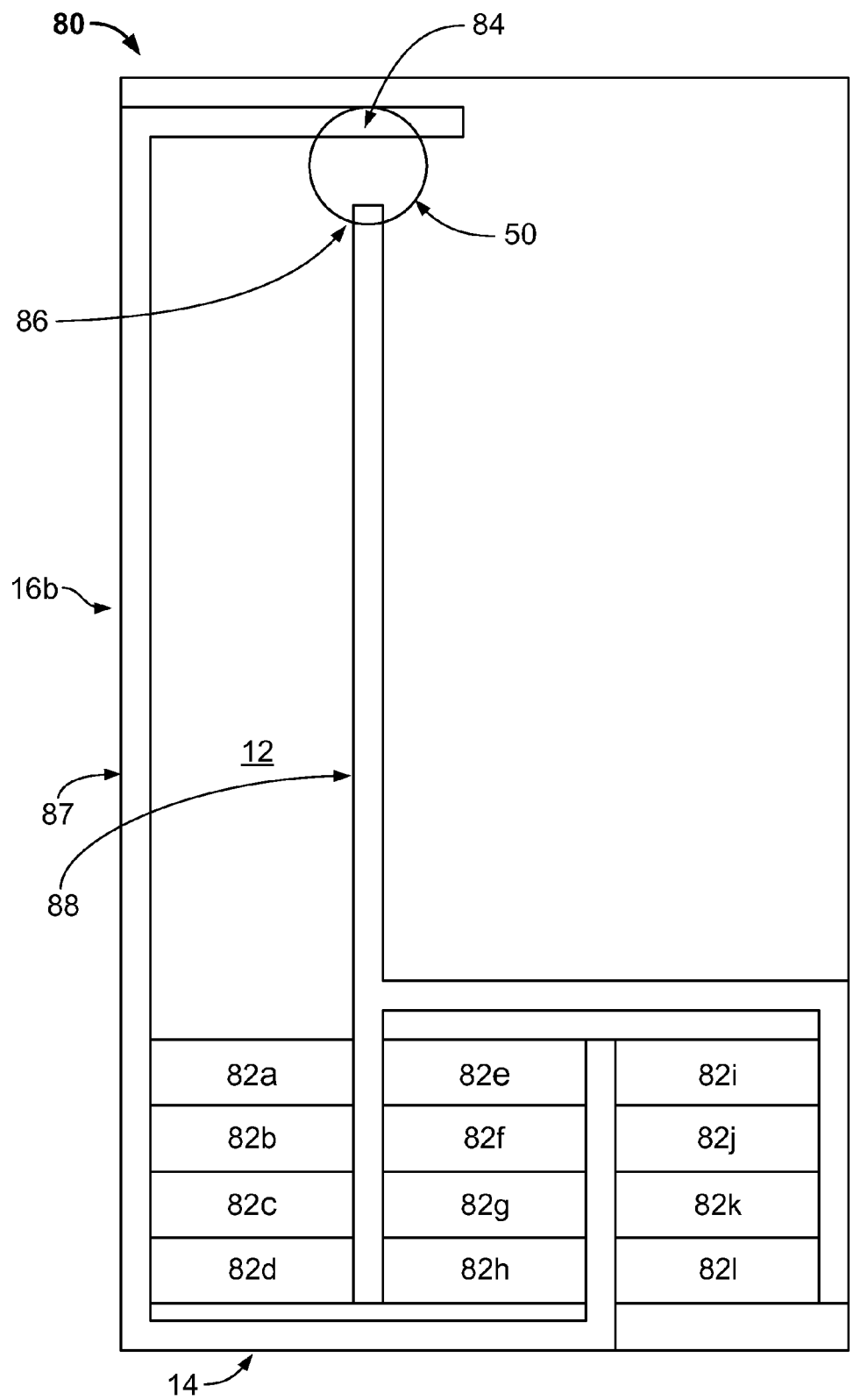
FIG. 1e is a top view of the base to be used in the electrochemical test sensor depicting a plurality of auto-calibration areas according to another embodiment.

Other examples of an electrochemical test sensor are shown in FIGS. 1d, 1e. FIGS. 1d, 1e depict an electrochemically-active layer without a lid. This would function in a generally similar manner as the electrochemical-active layer 16 shown and described with respect to FIG. 1b. The electrochemical test sensors of FIGS. 1d, 1e include a base, an electrochemically-active layer and a lid (not shown in FIGS. 1d, 1e).

Referring back to FIG. 1d, an electrochemical test sensor 70 includes the base 12, an electrochemically-active layer 16a and a lid (e.g., lid 20 of FIG. 1b). The electrochemical test sensor 70 includes the reactive or fluid-receiving area 50 discussed above. In one embodiment, an electrochemically-active layer 16a of FIG. 1d forms a plurality of electrodes 64, 66, a plurality of conductive leads or traces 67, 68 and a plurality of auto-calibration areas 62a-h. It is contemplated that the size and shape of the auto-calibration areas may vary from that depicted in FIG. 1d.

The plurality of electrodes of FIG. 1d includes at least a working electrode 64 and a counter electrode 66 according to this embodiment. The conductive leads 67, 68 assist in establishing electrical communication between the respective electrodes 64, 66 and the auto-calibration segments that will be eventually formed from the auto-calibration areas 62a-h. The auto-calibration segments or pads are electrically connected with meter contacts (not shown) and assist in conveying auto-calibration information of the analyte to the meter. It is also contemplated that the auto-calibration segments may also convey information to assist in determining the analyte concentration.

As discussed above, in addition to the working electrode 64 and the counter electrode 66, other electrodes may be formed on an electrochemical test sensor. It is contemplated that more or less electrodes may be formed in the electrochemical test sensor 70.

Referring back to FIG. 1e, an electrochemical test sensor 80 includes the base 12, an electrochemically-active layer 16b and a lid (not shown in FIGS. 1d, 1e).

The electrochemical test sensor 80 includes the reactive or fluid-receiving area 50 discussed above. In one embodiment, an electrochemically-active layer 16b of FIG. 1e forms a plurality of electrodes 84, 86, a plurality of conductive leads or traces 87, 88 and a plurality of auto-calibration areas 82a-l. It is contemplated that the size and shape of the auto-calibration areas may vary from that depicted in FIG. 1e.

The plurality of electrodes of FIG. 1e includes at least a working electrode 84 and a counter electrode 86 according to this embodiment. The conductive leads 87, 88 assist in establishing electrical communication between the respective electrodes 84, 86 and the auto-calibration segments that will be eventually formed from the auto-calibration areas 82a-l. The auto-calibration segments or pads are electrically connected with meter contacts (not shown) and assist in conveying auto-calibration information of the analyte to the meter. It is also contemplated that the auto-calibration segments may also convey information to assist in determining the analyte concentration.

As discussed above, in addition to the working electrode 84 and the counter electrode 86, other electrodes may be formed on an electrochemical test sensor. It is contemplated that more or less electrodes may be formed in the electrochemical test sensor 80. It is also contemplated that this interleaved pattern of the working and counter electrodes 87, 88 could be extends so as to add additional auto-calibration areas.

Figure 2A:
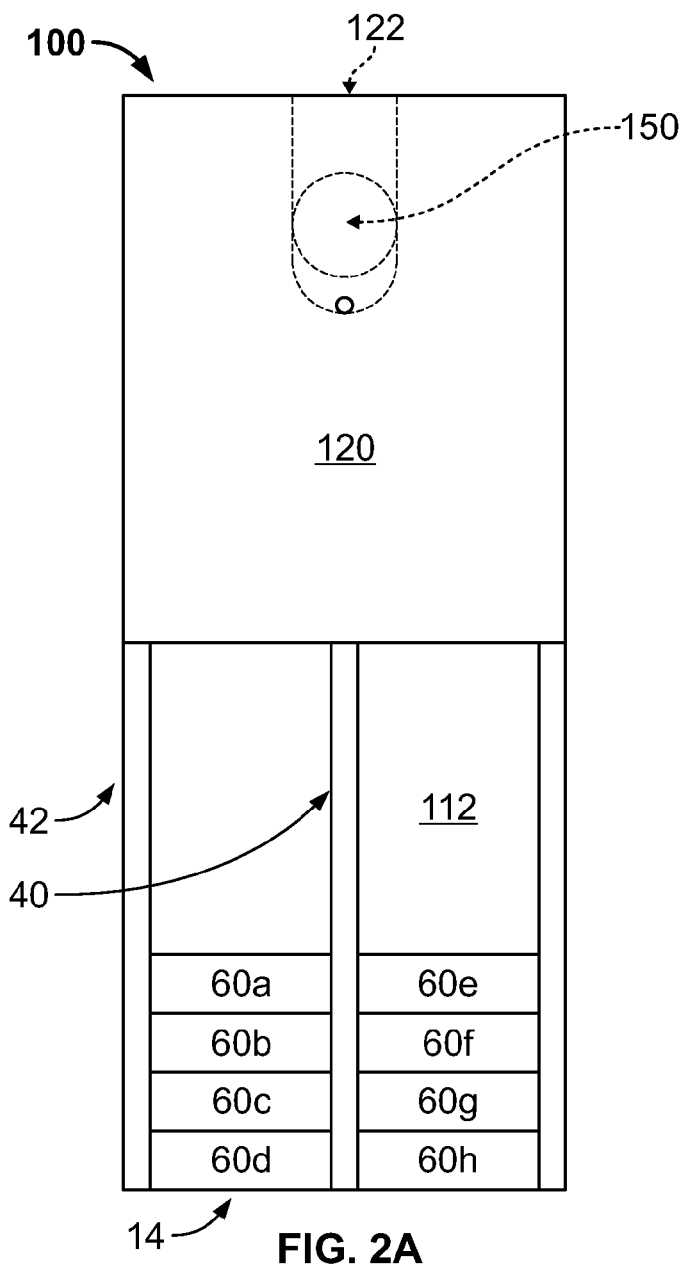
FIG. 2a is a top view of an electrochemical test sensor according to another embodiment.
Figure 2B:
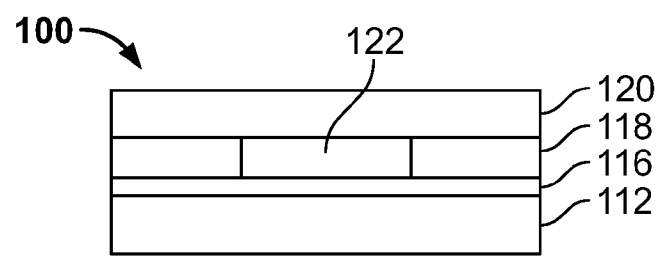

Another non-limiting example of an electrochemical test sensor is shown in FIGS. 2a, 2b. FIGS. 2a, 2b depict an electrochemical test sensor 100 that includes a base 112, an electrochemically-active layer 116, a spacer 118 and a lid 120. The base 112 and the electrochemically-active layer 116 may be the same or similar to the respective base 12 and the electrochemically-active layer 16 discussed above. A channel 122 (e.g., capillary channel) is formed when the base 112, the electrochemically-active layer 116, the spacer 118 and the lid 120 are attached to each other. The capillary channel 122 provides an enclosed flow path for introducing the sample into the test sensor 100 and eventually contacting the electrodes and, thus, forms a reaction zone.

The electrodes formed on the base 112 may be the same as described above with respect to the base 12. The electrodes include a counter and working electrode in one embodiment. In other embodiments, the electrodes may include additional electrodes such as the above discussed trigger electrode, detection electrode, hematocrit electrode, a second working electrode and other electrodes.

In one method, the electrochemical test sensors may be formed from ribbon strips. The ribbon strips may be made from processes such as a multiple-sheet process or a web process. For example, in an embodiment with a base, an electrochemically-active layer, spacer and lid, a base-ribbon strip, a spacer-ribbon strip and a lid-ribbon strip may be used. For improved efficiency, the electrochemical test sensors are generally formed after all of the ribbon strips have been attached.

According to one method, an electrochemical test sensor is formed. A base is provided and an electrochemically-active layer is placed thereon. The electrochemically-active layer is formed into the plurality of electrodes, plurality of conductive leads and the auto-calibration areas. A second layer is applied to assist in forming a channel in the test sensor. The channel assists in allowing a fluid sample to contact a reagent located therein.

The electrode pattern is generally from about 50 to about 500 Angstroms (Å) in thickness and, more typically, from about 150 to about 350 Angstroms (Å) in thickness. The electrochemically-active layer may be formed on the base by using, for example, physical vapor deposition (e.g., sputtering), coating, chemical vapor deposition (cvd), plating or printing.

The electrode pattern may be defined by using a mask and a laser such as, for example, an Excimer laser, solid state, YAG (singled, doubled or tripled frequency) or a carbon dioxide-based laser. One example of a mask is a chrome-on-glass mask in which a beam of light is only allowed to pass through selected areas.

According to another method, the electrode pattern may be formed with a laser using direct writing of the lines. In a method using a laser with direct writing of the lines, a laser beam of light is moved so as to define the electrode pattern. The laser may define, for example, the plurality of electrodes, the conductive leads and the auto-calibration areas. Lasers that produce a beam of energy capable of removing a layer and that can be moved to form an electrode pattern may be used in this method. Non-limiting examples of such lasers are carbon dioxide-based lasers and all yttrium-based lasers such as yttrium aluminum garnet (YAG) lasers.

In one process, the reagent may be applied to the electrode surfaces. The reagent may be applied to the electrode surface by, for example, gravure or screen printing, microdepositing (e.g., ink jet spraying) and coating (e.g., slot coating). In any embodiment, the reagent would need to contact the fluid sample, such as by using a capillary channel.

At least one of the base and the electrochemically-active layer is then attached to a second layer. In one embodiment, the second layer is a lid. As discussed above, the lid may be in the form of a ribbon strip. In another embodiment, the second layer is a spacer. As discussed above, the spacer may be in the form of a ribbon strip. According to another embodiment, the second layer may be a spacer-lid combination. The spacer-lid combination may be in the form of a ribbon strip (combination of spacer-ribbon strip and lid-ribbon strip) that has been previously formed before being attached to form an electrochemical test sensor. If ribbon strips are used, the test sensors may be excised using a mechanical punch or other methods.

The second layer (e.g., lid or spacer) may be attached to the base/electrode structure using, for example, a pressure-sensitive adhesive and/or a hot melt adhesive. Thus, the attachment uses pressure, heat or the combination thereof. It is contemplated that other materials may be used to attach the second layer and the base/electrode structure. It is also contemplated that the second layer and the base/electrode structure may be attached using ultrasonic energy or solvent welding.

Referring back to FIG. 1c, each of the plurality of auto-calibration areas 60a-h is adapted to be shorted to the respective counter conductive lead 40, the working conductive lead 42 or neither the conductive lead 40 or 42. After the auto-calibration areas are shorted or formed separately from one or more of the conductive leads, these will be referred to herein as an auto-calibration segment or pad. The auto-calibration segments that are not connected to either the counter conductive lead 40 or the working conductive lead 42 are referred to as "isolated" auto-calibration segments or pads. The actual calibration information is determined by which of the auto-calibration segments are electrically connected to which of the conductive leads, if any. Similarly, the auto-calibration areas 62a-h (FIG. 1d) and 82a-l (FIG. 1d) are adapted to be shorted to the respective counter conductive lead, the working conductive lead or neither of the conductive leads.

It is contemplated that the plurality of auto-calibration segments 60a-h may also be used to convey other information (besides auto-calibration information) related to the analyte. This may include, but is not limited to, information to assist in determining the analyte concentration. The auto-calibration segments or pads are adapted to electrically contact with meter contacts (not shown) of the meter. It is desirable for the auto-calibration segments to be used to perform such a function since this will eliminate the need for forming additional test sensor contacts that only perform this function. In one desirable method, each of the auto-calibration segments has a corresponding meter contact.

It also contemplated that other test-sensor contacts (separate from the auto-calibration segments) may be used to convey other information related to the analyte including, but not limited to, information to assist in determining the analyte concentration.

Referring to FIGS. 3a-c, non-limiting examples of auto-calibration segments that have been shorted to the counter conductive lead 40, the working conductive lead 42 or neither the conductive lead 40 nor 42 are respectfully depicted. FIGS. 3a-c show potential electrical connections, if any, of one of the auto-calibration areas 60 of FIG. 1c. Referring initially to FIG. 3a, the auto-calibration segment 75a is electrically connected to the working conductive lead 42 (see gap or space 78a). Thus, the auto-calibration segment 75a is not electrically connected to the counter conductive lead 40. Referring to FIG. 3b, the auto-calibration segment 75b is electrically connected to the counter conductive lead 40 (see gap or space 78b). Thus, the auto-calibration segment 75b is not electrically connected to the working conductive lead 42. Referring to FIG. 3c, the auto-calibration segment 75c is not electrically connected to the counter conductive lead 40 or the working conductive lead 42. Rather, the auto-calibration segment 75c is an isolated auto-calibration segment (see gaps 78a, 78b).

Various methods may be employed to form the auto-calibration segment to only the counter conductive lead 40, only the working conductive lead 42 or neither the conductive lead 40 or 42. For example, in one process, material may be ablated on three sides 80a, 80b, 80c to result in the auto-calibration segment 75a depicted in FIG. 3a. In another process, material may be ablated on a different three sides 80a, 80c, 80d to result in the auto-calibration segment 75b of FIG. 3b. In a further process, material may be ablated on four sides 80a-d to form the auto-calibration segment 75c of FIG. 3c.

Alternatively, the auto-calibration segments may be formed by other processes. For example, the auto-calibration may be formed by deposition including, but not limited to, screen printing or ink-jet printing.

Error checking of the auto-calibration information may be performed to verify whether a selected auto-calibration code is valid. Such error checking may be performed by several methods. In one embodiment, a valid code includes a predefined number of isolated auto-calibration segment(s) with the remaining auto-calibration segments being connected to either the counter or working conductive lead 40, 42. For example, a valid code may have exactly two isolated auto-calibration segments. Thus, in this process, the error-checking process simply determines whether there are exactly two isolated auto-calibration segments on the test sensors.

In another embodiment, a valid code may include having (a) at least two of the auto-calibration segments being isolated, (b) at least two of the auto-calibration segments being electrically connected to only the working conductive lead and (c) at least two of the auto-calibration segments being electrically connected to only the counter conductive lead. Thus, in this process, the error-checking process determines whether each of these criteria is satisfied.

One non-limiting example of a valid code using these parameters is shown in FIG. 4. FIG. 4 discloses an electrochemical test sensor 210 without a lid. The electrochemical test sensor 210 includes a base 212, an electrochemically-active layer 216 and reactive area 250. The electrochemically-active layer 216 forms a counter electrode 230, a working electrode 232, a counter conductive lead 240, a working conductive lead 242 and a plurality of auto-calibration segments 275a-h. Specifically, auto-calibration segments 275a, c, f, g are electrically connected to the working conductive trace 242 and, thus, to each other. Auto-calibration segments 275d, e, on the other hand, are electrically connected to the counter conductive trace 240 and, thus, to each other. The remaining auto-calibration segments 275b, h are isolated from the counter conductive trace 240 and the working conductive trace 242. It is contemplated that there are many valid auto-calibration codes that may be formed using these rules.

In a further embodiment, valid code may require (a) at least two of the auto-calibration segments being electrically connected to only the working conductive lead; and (b) at least two of the auto-calibration segments being electrically connected to only the counter conductive lead. Thus, in this process, the error-checking process determines whether these two criteria is satisfied. In yet another embodiment, error checking may be accomplished by requiring a pre-defined number of auto-calibration segments to be connected to a conductive lead.

It is contemplated that other valid code parameters may be implemented besides having an exact number or minimum number of at least one type of auto-calibration segment. It is contemplated that auto-calibration segments connected to the working conductive lead may be defined as a "0" and the auto-calibration segments connected to the conductive lead be defined as a "1" or vice versa, such that this binary number may be error checked with a checksum, CRC or check bit.

In another embodiment, error checking may be performed with enough auto-calibration segments by increasing the number of "groups" of connected segments. For example, such groups may include auto-calibration segments connected to working conductive group, counter conductive group, isolated group and a group of isolated segments connected to each other. It is also contemplated that resistance may be added as another variable to provide more potential auto-calibration information. For example, the auto-calibration segments may be made of different resistances such that a low, medium and/or high resistance per auto-calibration segment may be formed, which would provide more information per auto-calibration segment.

After the individual auto-calibration segments are formed on the electrochemical test sensor, they are adapted to be later read by a meter code-reading device that includes a plurality of code-reading contacts that corresponds with a respective individual auto-calibration segment. These code-reading contacts assist in determining how auto-calibration segments are electrically connected so as to ascertain the auto-calibration code to be used from that unique code. If the auto-calibration segments are connected to the working conductive lead and the counter conductive lead as discussed above, the meter code-reading device may in one embodiment use any auto-calibration segment connected to the working conductive lead and any auto-calibration segment connected to the counter conductive lead to perform the fluid analyte monitoring.

In one error-checking method, the code-reading device of the meter needs to determine how many isolated auto-calibration segments are present. If an auto-calibration segment is incorrectly coded or read as isolated, the number of isolated auto-calibration segments will be incorrect and the test sensor will be rejected. Similarly, if the code-reading device does not detect exactly two groups of auto-calibration segments electrically connected to each other, this indicates a coding error and the test sensor will be rejected. This requires at least two auto-calibration segments electrically connected to the working conductive lead and at least two auto-calibration segments electrically connected to the counter conductive lead, but no auto-calibration segments electrically connected to both the working conductive lead and the counter conductive lead. If any auto-calibration segment is connected to both the working conductive lead and the counter conductive lead, this will connect the two groups of auto-calibration segments, only one group of segments will be detected, and the test sensor will be rejected.

It is noted that for every valid code, there is a complement to that code that desirably should not be used. This is shown, for example, in FIGS. 5a, 5b with the electrochemical test sensor 310. The electrochemical test sensor 310 includes a plurality of auto-calibration segments 375a-f. FIGS. 5a, 5b both have isolated auto-calibration segments 375a, 375b in the same location. The other auto-calibration segments are reversed (i.e., in opposite orientations) in that FIG. 5a, for example, has an auto-calibration segment 375c electrically connected to the working conductive lead 342, while FIG. 5b has an auto-calibration segment 375c electrically connected to the counter conductive lead 340. To distinguish between the complements, an arbitrary rule may be used in which the first non-isolated auto-calibration segment must be connected to the working conductive lead.

Referring to another embodiment, an electrochemical test sensor 410 of FIG. 6a includes a plurality of auto-calibration areas 460a-h, a counter electrode 430, a working electrode 432, a reactive or fluid-receiving area 450, a counter conductive lead or trace 440 and a working conductive lead or trace 442. The plurality of auto-calibration areas 460a-h is staggered with respect to each other. It is contemplated that in other embodiments, a plurality of auto-calibration areas may be staggered in another pattern.

Figures 6B, 6C:
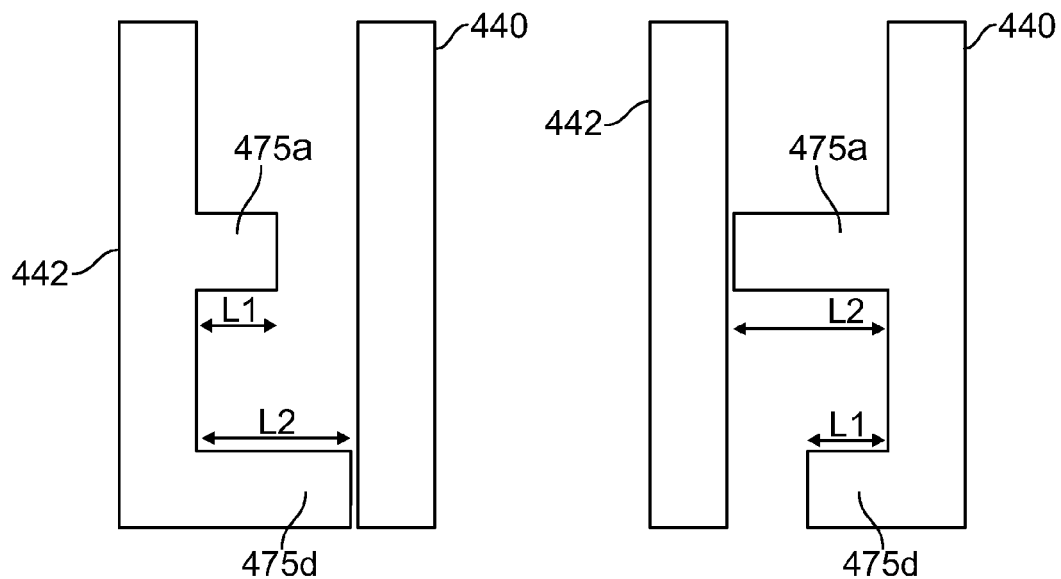
FIGS. 6b-6d are enlarged top views showing different types of auto-calibration segments having been formed in another method.
Figure 6D:
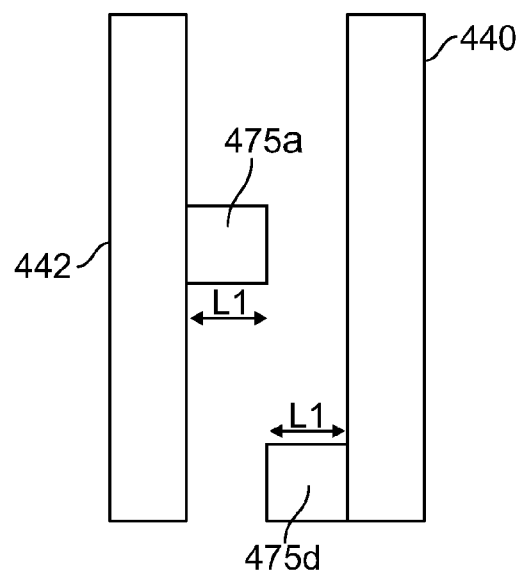

Referring to FIGS. 6b-6d, a portion of the auto-calibration areas is shown as being formed into a plurality of auto-calibration segments. Specifically, in FIG. 6b, auto-calibration segments 475a, d are shown of being different respective lengths L1, L2, but with both being electrically connected to the working conductive lead 442. Similarly, in FIG. 6c, auto-calibration segments 475a, d are shown of being different respective lengths L1, L2, but with both being electrically connected to the counter conductive lead 440. In FIG. 6d, auto-calibration segments 475a, d are of the same length L1, but are electrically connected to respective working conductive lead 442 and counter conductive lead 440.

Referring to FIGS. 7a, 7b are shown with specifically formed auto-calibration segments from the auto-calibration areas shown in FIG. 6a. Referring to FIG. 7a, an electrochemical test sensor 455 is depicted that includes isolated auto-calibration segments 475a,b that are not electrically connected to either the counter conductive lead 440 or the working conductive lead 442. Auto-calibration segments 475c, e, g are electrically connected to the working conductive lead 442. Auto-calibration segments 475d, f, h are electrically connected to the counter conductive lead 440. In the complement of FIG. 7a, the electrochemical test sensor 465 has the isolated auto-calibration segments 475a,b that are not electrically connected to either the counter conductive lead 442 or the working conductive lead 440. The electrochemical test sensor 465 of FIG. 7b also has the auto-calibration segments 475c, e, g being electrically connected to the counter conductive lead 440 and auto-calibration segments 475d, f, h are electrically connected to the working conductive lead 442.

Figure 8:
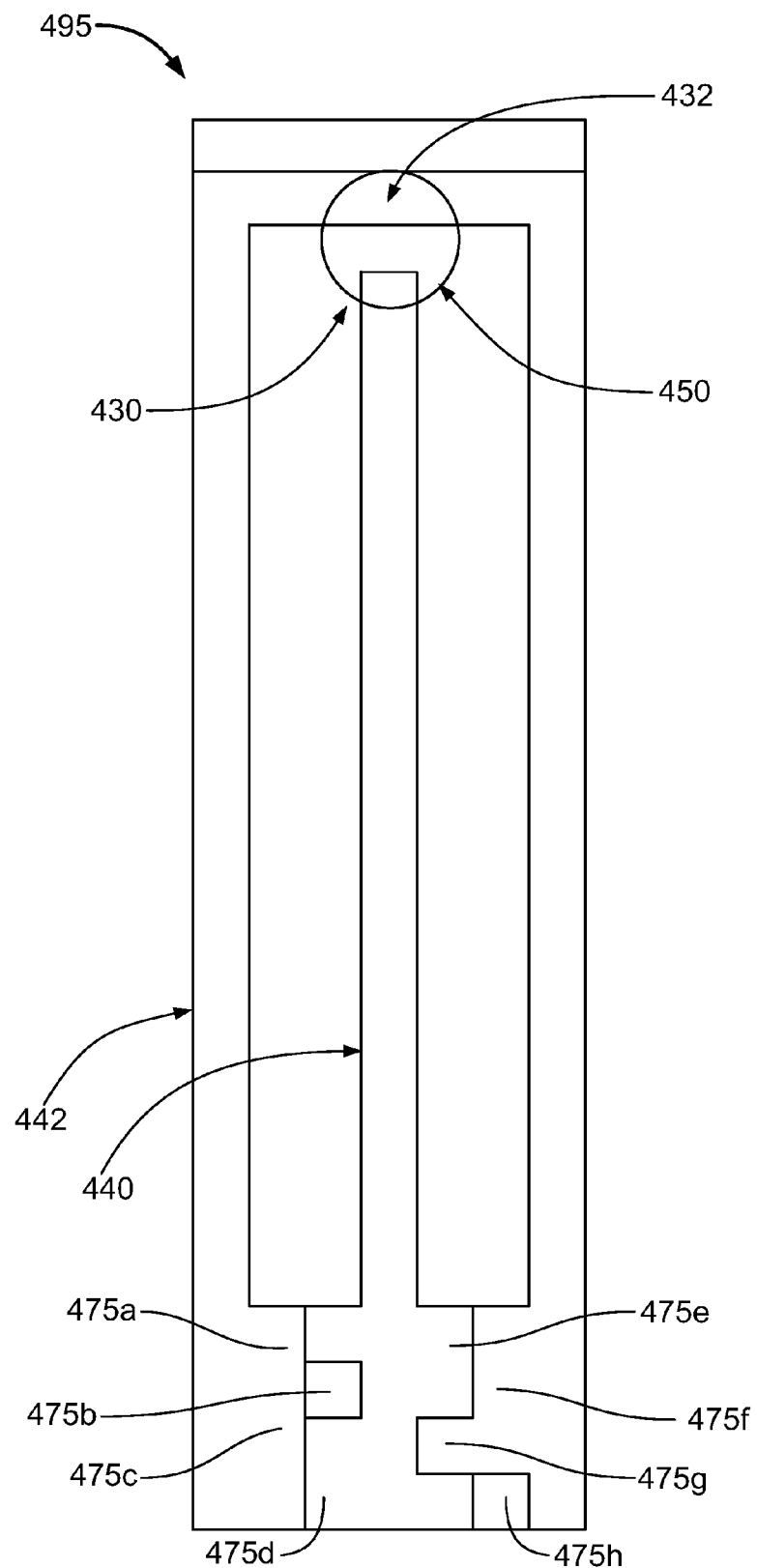
FIG. 8 is a top view of an electrochemical test sensor without a lid depicting auto-calibration segments according to one embodiment.

In another embodiment, an electrochemical test sensor 495 of FIG. 8 forms different auto-calibration segments. The electrochemical test sensor 495 includes isolated auto-calibration segments 475b,h that are not electrically connected to either the counter conductive lead 440 or the working conductive lead 442. Auto-calibration segments 475a, c, f, g are electrically connected to the working conductive lead 442. Auto-calibration segments 475d, e are electrically connected to the counter conductive lead 440.

Figure 9A:
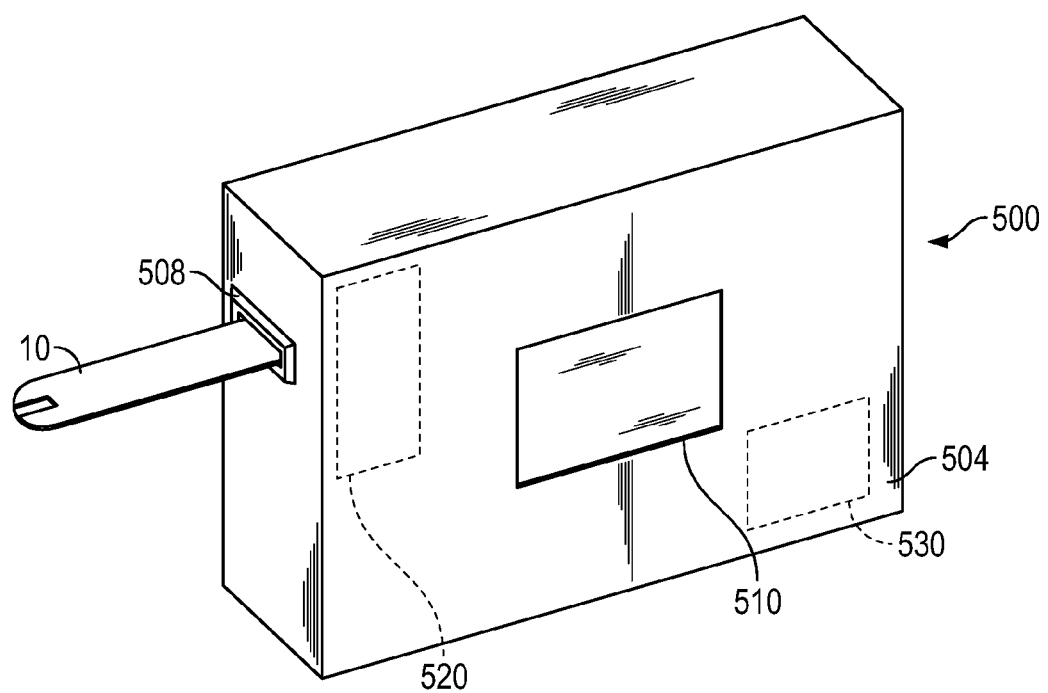
FIG. 9a is an isometric view of a meter according to one embodiment that is adapted to receive the test sensors of FIGS. 1-8.

The test sensors are adapted to be used in a meter or instrument. One non-limiting example of a meter or instrument that may be used with the test sensors of FIGS. 1-8 is shown in FIG. 9a. FIG. 9a depicts a single-sensor meter or instrument 500. The single-sensor meter 500 comprises a housing 504 that forms a test-sensor opening 508 of sufficient size to receive the second opposing end of a test sensor (e.g., second opposing end 14 of the test sensor 10 in FIG. 1a). A test sensor in one method is adapted to be placed manually into the test-sensor opening 508. The meter uses, for example, the appropriate program number from the meter software after determining the end shape of the test sensor. The device housing may comprise an LCD screen 510 that displays, for example, analyte concentrations. The meter 500 further includes a processor 520 and a memory 530.

Figure 9B:
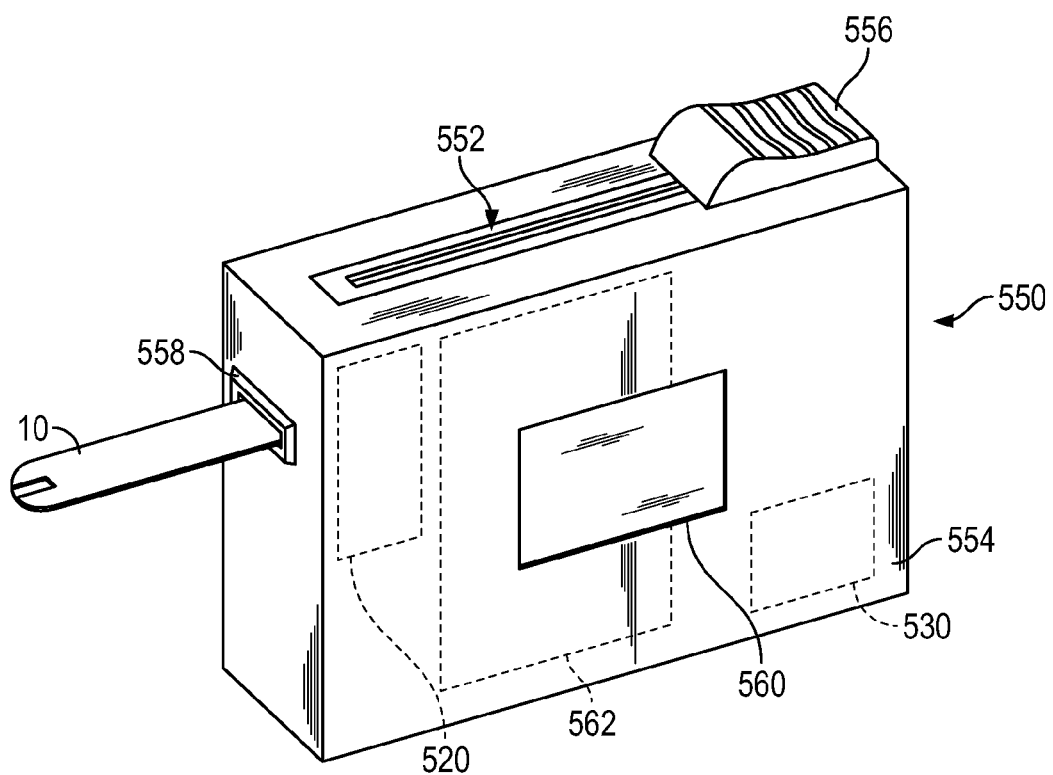
FIG. 9b is an isometric view of a meter according to another embodiment that is adapted to receive a cartridge.

Another non-limiting example of a meter or instrument that may be used with the test sensors of FIGS. 1-8 is shown in FIG. 9b. FIG. 9b depicts a single-sensor meter or instrument 550. The single-sensor meter 550 comprises a sliding assembly 552 and housing 554. The sliding assembly 552 includes a slider 556 and a test sensor-extraction mechanism (not shown) that is attached to the slider 556. The housing 554 also forms a test-sensor opening 558 of sufficient size to receive the second opposing end of a test sensor (e.g., second opposing end 14 of the test sensor 10). The device housing may comprise an LCD screen 560 that displays, for example, analyte concentrations. In one method, the test sensor is adapted to be extracted from a test-sensor cartridge 562 and automatically placed in position to determine the auto-calibration of the test sensor. The meter 550 further includes the processor 570 and a memory 580. It is contemplated that other meters or instruments may be used with the test sensors of FIGS. 1-8.

The meter or instrument (e.g., meters 500, 550) is adapted to detect the auto-calibration information after it is received in the test-sensor opening. The meter or instrument is then adapted to apply the proper auto-calibration information thereto.

The calibration information referred to herein may be any information that may be used by a meter or instrument. For example, the calibration information may be a program auto-calibration number that relates to a slope and intercept of calibration lines for the test sensor lot or batch. In addition to calibration information, other information may be contained such an analyte type, geographical region or country, manufacturing or expiry date, and/or chemistry version.

Process A

A method of making an electrochemical test sensor adapted to assist in determining information relating to an analyte in a fluid sample, the method comprising the acts of:
providing a base;
providing a second layer to assist in forming a channel;
providing a plurality of electrodes on the base, the plurality of electrodes including a working electrode and a counter electrode;
providing a working conductive lead that is electrically connected to the working electrode;
providing a counter conductive lead that is electrically connected to the counter electrode;
providing a reagent formed in the channel;
providing auto-calibration information of the test sensor by forming a plurality of auto-calibration segments to be connected to one of the following: the working conductive lead, the counter conductive lead, or neither of the conductive leads, and wherein at least one of the plurality of auto-calibration segments is connected to the working conductive lead and at least one of the plurality of auto-calibration segments is connected to the counter conductive lead.

Process B

The method of alternative process A wherein the second layer is a lid and the lid assisting in forming a channel in which to receive the fluid, the channel including the reagent.

Process C

The method of alternative process A wherein the second layer is a spacer and wherein the test further includes a lid, the spacer and lid assisting in forming a channel in which to receive the fluid.

Process D

The method of alternative process A wherein the reagent includes glucose oxidase or glucose dehydrogenase.

Process E

The method of alternative process A wherein at least one of the plurality of auto-calibration leads is connected to neither the working conductive lead nor the counter conductive lead.

Process F

The method of alternative process A wherein providing the plurality of electrodes and the conductive leads on the base includes placing an electrochemically-active layer on the base and laser-ablating the electrochemically-active layer.

Process G

The method of alternative process A wherein the channel is a capillary channel.

Process H

The method of alternative process A wherein providing the plurality of electrodes and the conductive leads on the base includes printing the plurality of electrodes and the conductive leads on the base.

Process I

The method of alternative process A wherein providing auto-calibration information of the test sensor by forming the plurality of auto-calibration segments including providing a plurality of auto-calibration areas connected to the working and counter conductive areas and shorting the same.

Process J

The method of alternative process A wherein the plurality of auto-calibration segments includes at least six auto-calibration segments.

Process K

The method of alternative process J wherein the plurality of auto-calibration segments includes at least eight auto-calibration segments.

Embodiment L

An electrochemical test sensor being adapted to assist in determining information relating to an analyte in a fluid sample, the test sensor comprising:

a base including a plurality of electrodes, a working conductive lead and a counter conductive lead thereon, the plurality of electrodes including a working electrode and a counter electrode; and a second layer to assist in forming a channel, the channel including a reagent therein;

wherein auto-calibration information of the test sensor is determined by including the use of a plurality of auto-calibration segments connected to one of the following: the working conductive lead, the counter conductive lead, or neither of the conductive leads, at least one of the plurality of auto-calibration segments being connected to the working conductive lead and at least one of the plurality of auto-calibration segments being connected to the counter conductive lead.

Embodiment M

The test sensor of alternative embodiment L wherein the second layer is a lid and the lid assisting in forming a channel in which to receive the fluid, the channel including the reagent.

Embodiment N

The test sensor of alternative embodiment L wherein the second layer is a spacer and wherein the test further includes a lid, the spacer and lid assisting in forming a channel in which to receive the fluid.

Embodiment O

The test sensor of alternative embodiment L wherein the reagent includes glucose oxidase or glucose dehydrogenase.

Embodiment P

The test sensor of alternative embodiment L wherein at least one of the plurality of auto-calibration leads is connected to neither the working conductive lead nor the counter conductive lead.

Embodiment Q

The test sensor of alternative embodiment L wherein the channel is a capillary channel.

Embodiment R

The test sensor of alternative embodiment L wherein the plurality of auto-calibration segments includes at least six auto-calibration segments.

Embodiment S

The test sensor of alternative embodiment L wherein the plurality of auto-calibration segments includes at least eight auto-calibration segments.

What is claimed is:

1. A method of making an electrochemical test sensor adapted to assist in determining information relating to an analyte in a fluid sample, the method comprising the acts of:
   providing a base;
   providing a second layer to assist in forming a channel;
   providing a plurality of electrodes on the base, the plurality of electrodes including a working electrode and a counter electrode;
   providing a working conductive lead that is electrically connected to the working electrode;
   providing a counter conductive lead that is electrically connected to the counter electrode;
   providing a reagent formed in the channel; and
   providing information of the test sensor by forming a plurality of information segments to be connected to one of the following: the working conductive lead, the counter conductive lead, or neither of the conductive leads, and wherein at least one of the plurality of information segments is connected to the working conductive lead and at least one of the plurality of information segments is connected to the counter conductive lead;
   wherein each of a first plurality of information areas is located between a first portion of the working conductive lead and a portion of the counter conductive lead and each of a second plurality of information areas is located between a second portion of the working conductive lead and a portion of the counter conductive lead, the location of the first plurality of information areas being different from the second plurality of information areas;
   wherein each of the first plurality of information areas is located on an opposing side of the counter conductive lead as compared to each of the second plurality of information areas;
   wherein the working conductive lead extends along at least a portion of two peripheries of the electrochemical test sensor;
   wherein the information is an analyte type, a geographical region, a country, a manufacturing date, an expiry date, a chemistry version or any combination thereof.

2. The method of claim 1 wherein the second layer is a lid, the lid assisting in forming a channel in which to receive the fluid, the channel including the reagent.

3. The method of claim 1 wherein the second layer is a spacer and wherein the test further includes a lid, the spacer and lid assisting in forming a channel in which to receive the fluid.

4. The method of claim 1 wherein the reagent includes glucose oxidase or glucose dehydrogenase.

5. The method of claim 1 wherein at least one of the plurality of information segments is connected to neither the working conductive lead nor the counter conductive lead.

6. The method of claim 1 wherein providing the plurality of electrodes and the conductive leads on the base includes placing an electrochemically-active layer on the base and laser-ablating the electrochemically-active layer.

7. The method of claim 1 wherein providing information of the test sensor by forming the plurality of information segments includes providing a plurality of information areas connected to the working and counter conductive areas and shorting the same.

8. The method of claim 1 wherein the information is the analyte type.

9. The method of claim 1 wherein the information is the geographical region or the country.

10. The method of claim 1 wherein the information is the manufacturing date or the expiry date.

11. The method of claim 1 wherein the information is the chemistry version.

12. The method of claim 1 wherein the working conductive lead is generally in a U-shape configuration.

13. An electrochemical test sensor being adapted to assist in determining information relating to an analyte in a fluid sample, the test sensor comprising:

a base including a plurality of electrodes, a working conductive lead and a counter conductive lead thereon, the plurality of electrodes including a working electrode and a counter electrode; and a second layer to assist in forming a channel, the channel including a reagent therein;

wherein information of the test sensor is determined by using a plurality of information segments connected to one of the following: the working conductive lead, the counter conductive lead, or neither of the conductive leads;

wherein at least one of the plurality of information segments being connected to the working conductive lead and at least one of the plurality of information segments being connected to the counter conductive lead;

wherein each of a first plurality of information areas is located between a first portion of the working conductive lead and a portion of the counter conductive lead and each of a second plurality of information areas is located between a second portion of the working conductive lead and a portion of the counter conductive lead, the location of the first plurality of information areas being different from the second plurality of information areas;

wherein each of the first plurality of information areas is located on an opposing side of the counter conductive lead as compared to each of the second plurality of information areas;

wherein the working conductive lead extends along at least a portion of two peripheries of the electrochemical test sensor;

wherein the information is an analyte type, a geographical region, a country, a manufacturing date, an expiry date, a chemistry version or any combination thereof.

14. The test sensor of claim 13 wherein the second layer is a lid, the lid assisting in forming a channel in which to receive the fluid, the channel including the reagent.

15. The test sensor of claim 13 wherein the second layer is a spacer and wherein the test further includes a lid, the spacer and lid assisting in forming a channel in which to receive the fluid.

16. The test sensor of claim 13 wherein the reagent includes glucose oxidase or glucose dehydrogenase.

17. The test sensor of claim 13 wherein at least one of the plurality of information segments is connected to neither the working conductive lead nor the counter conductive lead.

18. The test sensor of claim 13 wherein the plurality of information segments includes at least six information segments.

19. The test sensor of claim 13 wherein the working conductive lead is generally in a U-shape configuration.

20. The test sensor of claim 13 wherein the information is the analyte type.

21. The test sensor of claim 13 wherein the information is the geographical region or the country.

22. The test sensor of claim 13 wherein the information is the manufacturing date or the expiry date.

23. The test sensor of claim 13 wherein the information is the chemistry version.

24. A method of making an electrochemical test sensor adapted to assist in determining information relating to an analyte in a fluid sample, the method comprising the acts of:
providing a base;
providing a second layer to assist in forming a channel;
providing a plurality of electrodes on the base, the plurality of electrodes including a working electrode and a counter electrode;

providing a working conductive lead that is electrically connected to the working electrode;
providing a counter conductive lead that is electrically connected to the counter electrode;
providing a reagent formed in the channel; and
providing information of the test sensor by forming a plurality of information segments to be connected to one of the following: the working conductive lead, the counter conductive lead, or neither of the conductive leads, and wherein at least one of the plurality of information segments is connected to the working conductive lead and at least one of the plurality of information segments is connected to the counter conductive lead;
wherein each of a first plurality of information areas is located between a first portion of the working conductive lead and a portion of the counter conductive lead and each of a second plurality of information areas is located between a second portion of the working conductive lead and the portion of the counter conductive lead, the location of the first plurality of information areas being different from the second plurality of information areas;
wherein each of the first plurality of information areas is located on an opposing side of the portion of the counter conductive lead as compared to each of the second plurality of information areas;
wherein the working conductive lead is generally in a U-shape configuration;
wherein the information is an analyte type, a geographical region, a country, a manufacturing date, an expiry date, a chemistry version or any combination thereof.

25. An electrochemical test sensor being adapted to assist in determining information relating to an analyte in a fluid sample, the test sensor comprising:
a base including a plurality of electrodes, a working conductive lead and a conductive lead thereon, the plurality of electrodes including a working electrode and a counter electrode; and
a second layer to assist in forming a channel, the channel including a reagent therein;
wherein information of the test sensor is determined by using a plurality of information segments connected to one of the following: the working conductive lead, the counter conductive lead, or neither of the conductive leads;
wherein at least one of the plurality of information segments being connected to the working conductive lead and at least one of the plurality of information segments being connected to the counter conductive lead;
wherein each of a first plurality of information areas is located between a first portion of the working conductive lead and a portion of the counter conductive lead and each of a second plurality of information areas is located between a second portion of the working conductive lead and the portion of the counter conductive lead, the location of the first plurality of information areas being different from the second plurality of information areas;
wherein each of the first plurality of information areas is located on an opposing side of the portion of the counter conductive lead as compared to each of the second plurality of information areas;
wherein the working conductive lead is generally in a U-shape configuration;
wherein the information is an analyte type, a geographical region, a country, a manufacturing date, an expiry date, a chemistry version or any combination thereof.

* * * * *